US00PP12298P2

(12) United States Plant Patent
Piscator

(10) Patent No.: US PP12,298 P2
(45) Date of Patent: Dec. 18, 2001

(54) POINSETTIA PLANT NAMED 'FISSON GOLD'

(75) Inventor: Jens Helmut Piscator, Moncarapacho (PT)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/590,691

(22) Filed: Jun. 9, 2000

(51) Int. Cl.[7] ..... A01H 5/00
(52) U.S. Cl. ..... Plt./306
(58) Field of Search ..... Plt./306

(56) References Cited

FOREIGN PATENT DOCUMENTS

| | | |
|---|---|---|
| 99-1556 | 1/1999 | (CA) . |
| EUP 210 | 9/1998 | (DE) . |
| 99/1192 | 8/1999 | (EP) . |
| 11746 | 5/1999 | (JP) . |
| 0 660/0 689 | 4/1999 | (PL) . |

OTHER PUBLICATIONS

UPOV–ROM GTITM Computer Database 2000/05, GTI JOUVE Retrieval Software, citation(s) for 'Fisson Gold' Oct. 10, 2000.*

* cited by examiner

*Primary Examiner*—Bruce R. Campell
*Assistant Examiner*—A H. Para
(74) *Attorney, Agent, or Firm*—Foley & Lardner

(57) ABSTRACT

A new and distinct cultivar of Poinsettia plant named 'Fisson Gold' characterized by having light to medium-pink bract color; medium-sized, star-shaped inflorescence with distinctly pointed bracts; bicolored foliage with dark-green main color and bright yellow-colored center of the leaves; light, slightly yellowish stems and petioles without chlorophyll but with strong reddish infusion in parts; and weak growth and compact, low plant habit.

2 Drawing Sheets

BACKGROUND OF THE INVENTION

The present invention relates to a new and distinct cultivar of Poinsettia plant known by the cultivar name 'Fisson Gold', and botanically known as *Euphorbia pulcherrima*.

'Fisson Gold' was derived from a naturally-occurring mutation of the variety 'Fissonosa' (U.S. Plant Pat. No. 10,182). 'Fisson Gold' was discovered by the inventor, Jens Helmut Piscator, among a group of stock plants in Olhao, Portugal, in 1996. 'Fissonosa' is characterized by its pink-colored bracts with strong, pointed lobes, uniform dark-green foliage and relatively compact, round plant habit.

'Fisson Gold' originated from a single plant displaying a branch with variegated foliage. Cuttings were taken from this branch, rooted and grown out by the inventor. One of the resulting plants, which was completely mutated, was taken to Hillscheid, Germany, in winter 1997/98, for further examination. Since the bicolored foliage looked attractive even without flowers, the plant was chosen and was used as a stock plant for asexual propagation.

Horticultural examination of the variety starting in the late summer of 1998, and continuing thereafter, has demonstrated that the combination of characteristics as herein disclosed for 'Fisson Gold' are firmly fixed and retained through successive generations of asexual reproduction.

BRIEF DESCRIPTION OF THE INVENTION

The following traits have been repeatedly observed and are determined to be basic characteristics of 'Fisson Gold' which in combination distinguish this Poinsettia as a new and distinct cultivar:

1. Light to medium-pink bract color;
2. Medium-sized, star-shaped inflorescence with distinctly pointed bracts;
3. Bicolored foliage with dark-green main color and bright, yellow-colored center of the leaves;
4. Light, slightly yellowish stems and petioles without chlorophyll but with strong reddish infusion in parts; and
5. Weak growth and compact, low plant habit.

'Fisson Gold' has not been observed under all possible environmental conditions. The phenotype may vary significantly with variations in environment such as temperature, light intensity and daylength without any change in genotype. The following observations, measurements and comparisons describe plants grown in Hillscheid, Germany, under greenhouse conditions which approximate those generally used in commercial practice.

Of the many commercial cultivars known to the inventor, the most similar in comparison to 'Fisson Gold' is the parental cultivar 'Fissonosa'. Reference is made to attached Chart A which compares certain characteristics of 'Fisson Gold' to those same characteristics of 'Fissonosa'.

Chart A

| | 'Fisson Gold' | 'Fissonosa' |
|---|---|---|
| Plant height | 26.6 cm | 39.1 cm |
| No. of branches | 5.8 | 9.3 |
| Size of leaf | 11.5 cm | 16.5 cm |
| Size of bract | 9.1 cm | 13.2 cm |

-continued

| Chart A | | |
|---|---|---|
| | 'Fisson Gold' | 'Fissonosa' |
| Foliage color | bicolored, dark-green and yellow | uniform dark-green |

In contrast to 'Fissonosa', which has uniform, dark-green colored leaves, 'Fisson Gold' has distinctly variegated foliage with a chlorophyll-free, yellowish to golden-colored central area of the leaf, and yellowish stems and petioles. Due to the lack of chlorophyll, the infusion of anthocyanin, though basically not stronger than with the parental variety, creates a distinct pink to orange hue on parts of stems and petioles. Furthermore, 'Fisson Gold' grows considerably more slowly, and therefore develops fewer branches and has a considerably smaller and lower plant habit when grown under the same cultivation schedule.

BRIEF DESCRIPTION OF THE DRAWING

The accompanying color drawings show typical inflorescence and foliage of a plant of 'Fisson Gold', with colors being as true as possible with illustrations of this type.

The first drawing shows a top view of a group of three small potted plants.

The second drawing shows a close-up of the view of the inflorescence of cyme.

DETAILED BOTANICAL DESCRIPTION

The plants described were grown in a greenhouse in Langley, British Columbia, Canada, in the fall of 1999. Rooted cuttings were planted into 15-cm pots on August 9, and were pinched on August 19, leaving 8 nodes. The minimum temperature was 22° C. until October 10, 18.5° C. to mid-November, and lower thereafter. The plants initiated flowers under artificial, short-day conditions, blackout, from September 19 to October 1, and grew under natural, short-day conditions thereafter.

Observations and measurements were mainly taken on November 23, at the beginning of full flowering. In the following description, color references are made to The Royal Horticultural Society (R.H.S.) Colour Chart. The color values were determined indoors in a north light.

Classification:

*Botanical.*—*Euphorbia pulcherrima.*

*Commercial.*—Poinsettia, cv 'Fisson Gold'.

Parentage: Naturally-occurring mutation of 'Fissonosa'.

Plant:

*Form.*—Shrub, self-branching.

*Growth habit.*—Weak growth, compact habit, pinched plants are low and fairly round in shape.

*Height* (*with pot*).—26.7 cm.

*Width.*—21.5 cm.

*Average number of branches.*—5.8.

*Average number of inflorescences.*—Approximately 5.

*Stem color.*—Basic color is yellowish-white, about RHS 10C, partly infused with anthocyanin of varying intensity; the resulting color ranges from salmon-orange to pink or rose, about RHS 39B to RHS 50B.

*Blooming habit.*—Begin under natural, short-day conditions in fall: Botanically (cyathia open): Around December 1. Commercially (bracts colored, marketable): Around December 1.

*Flowering response time.*—About 9.5 weeks.

Foliage:

*Shape.*—Basal part roughly triangular with acute base, strong, pointed lobes and acuminate tip. Smaller leaves without lobes are broad elliptically shaped.

*Margin.*—Entire, apart from the lobes.

*Texture.*—Upper surface: Mainly smooth and flat, only weakly veined; color of veins is yellowish-white, RHS 10C–D. Lower surface: Flat and smooth, except for the slightly protruding midrib and finer side veins, which are arranged in a pinnate pattern; the vein color is near RHS 10D.

*Size.*—Leaf blade length is 11.50 cm; leaf blade width is 7.35 cm; petiole length is 3.75 cm.

*Color.*—Generally dark-green with an irregularly-shaped, yellow central area. Mature foliage, near margin: Upper surface is RHS 139A–137A. Under surface is RHS 137B. Variegation, central area: Upper side is RHS 6A. Under side is RHS 10A.

*Petiole color.*—Upper side is salmon-pink, RHS 41C–D. Lower side is whitish, RHS 10D.

*Aspect.*—Petioles are horizontally directed, while the leaf blades show slightly downward.

Flowering description:

*Whole inflorescence.*—Star-shaped, almost flat, with the bracts horizontally directed or slightly downward.

*Keeping quality.*—Relatively good.

*Diameter.*—17.5 cm.

*Bract shape.*—Usually roughly triangular with acute bases, acuminate tips and distinctly lobed with pointed tips; the smaller, upper bracts are elliptically-shaped and almost without lobes.

*Bract texture.*—Flat and smooth, the veins are arranged in a pinnate pattern and are hardly visible on the surface; as bracts mature, veins may create a slightly rugose pattern. The vein color corresponds closely to the bract color, except for the base of the midrib, which is dull-red, about RHS 46B–53C.

*Size of bract.*—Largest true bract is 9.1 cm long and 6.5 cm wide; petiole is 1.5 cm long.

*Color.*—Generally light-pink to pink, with the youngest bracts most intense in color. Upper surface: Lower bracts are RHS 52B or lighter; upper, smaller bracts are RHS 50A–52A. Lower surface: RHS 51B–C.

*Petiole color.*—RHS 53C–D.

*Cyme.*—Diameter is 20 mm, usually few, about 5–10 cyathia in a narrow cluster. Retention of the cyathia: 15–20 days under winter conditions in central Europe with natural low light. Cyathium diameter: 5 mm. Cyathium color: Mainly yellowish-white, RHS 10C, with light-green patches, RHS 149A; top is pink to rose-red, RHS 52A–B. Nectar cups: Small to medium-sized, bright yellow in color, usually no, or only very little, anthocyanin coloring at the margin.

Reproductive organs:

*Stamens.*—Light-pink filaments, fertile with yellow pollen, approximately 5–10 in a tight cluster.

*Pistil.*—Style and stigma are pink; 6-lobed stigma.

*Ovaries.*—Yellow/light-green (same color as cyathium), triangular, 3 ovules.

*Fruit/seed.*—None observed.

Rooting: Not very fast, about 24 days.

Disease resistance: Typical, no special observation made.

I claim:

1. A new and distinct Poinsettia plant named 'Fisson Gold', substantially as illustrated and described.

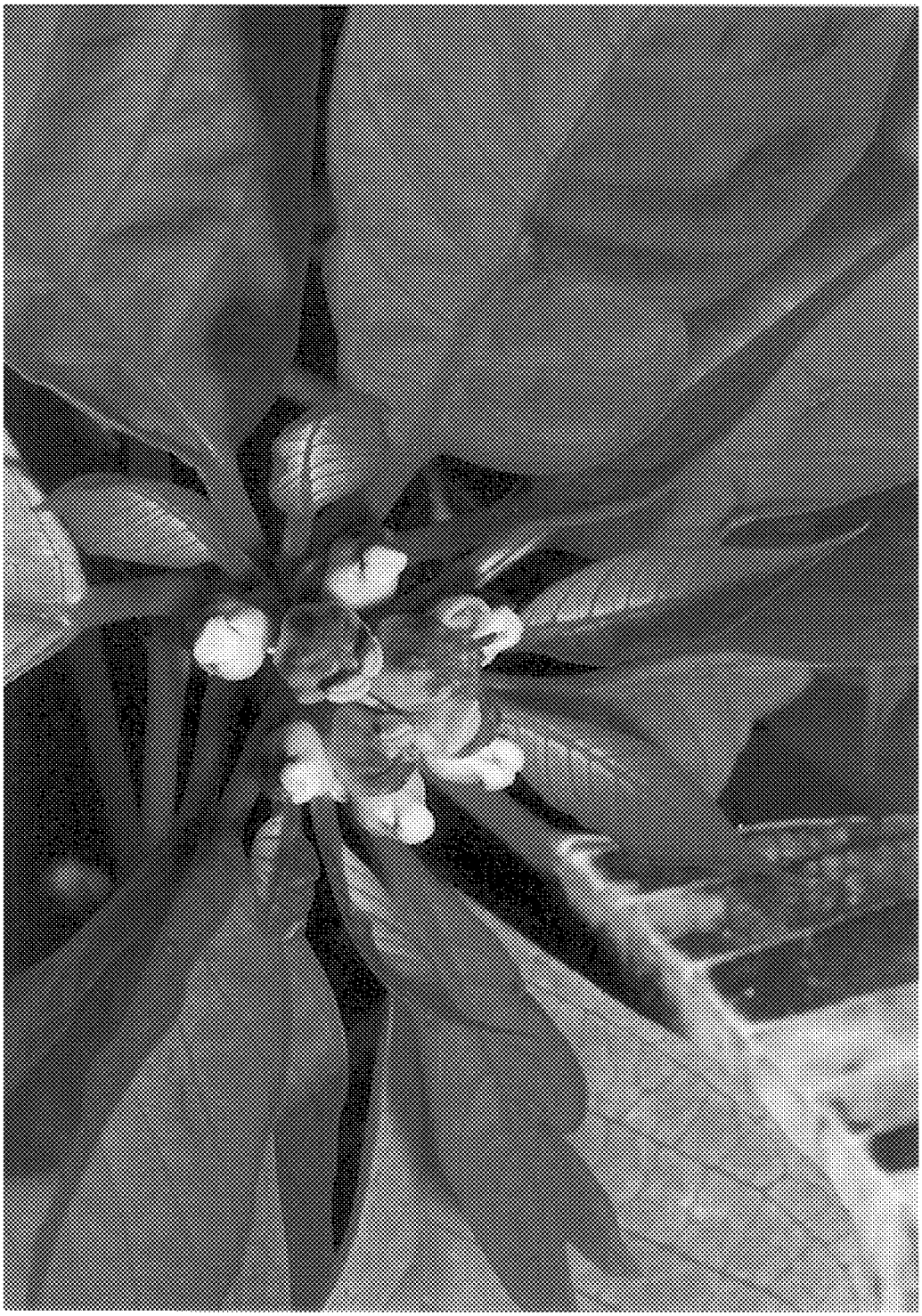

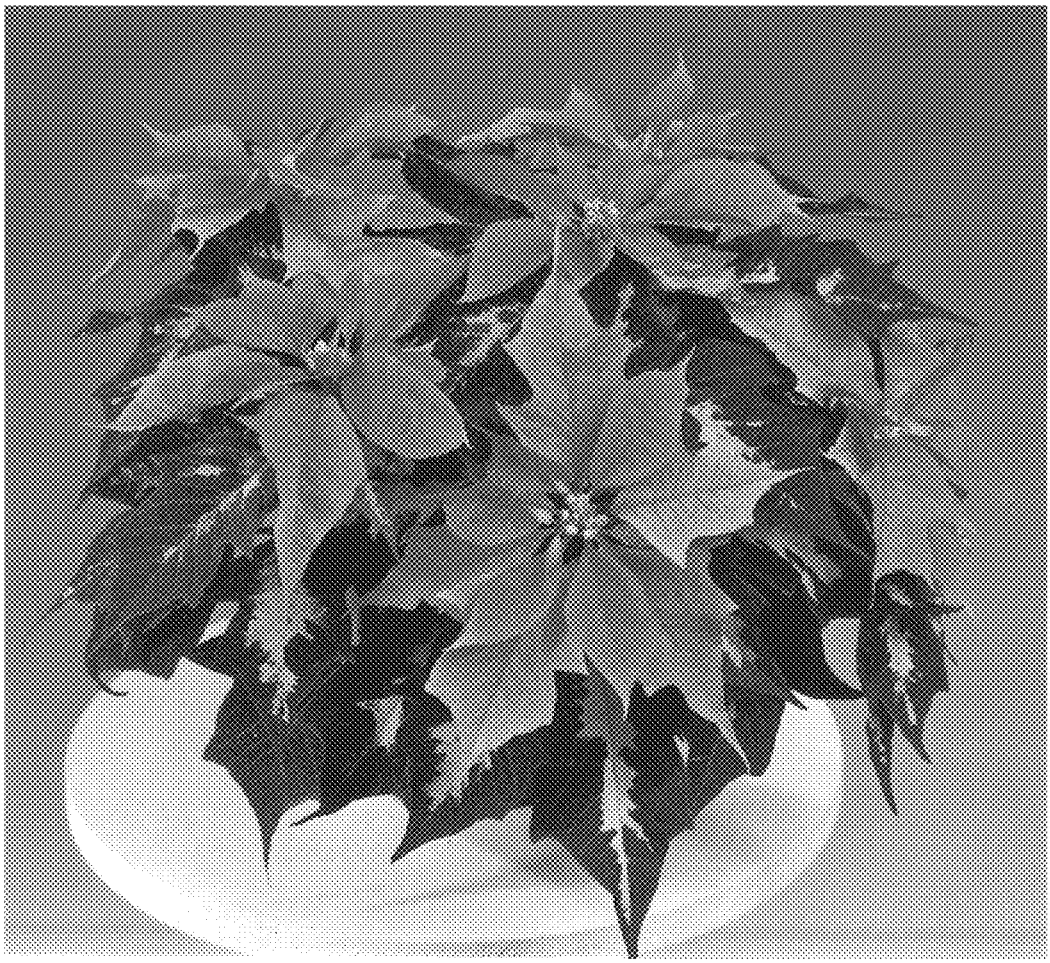

* * * * *